United States Patent
Yeh

(10) Patent No.: US 6,485,463 B1
(45) Date of Patent: Nov. 26, 2002

(54) MEDICINE DELIVERY APPARATUS WITH FLAT RESERVOIR

(76) Inventor: Show-Way Yeh, 21701 Stevens Creek Blvd., Cupertino, CA (US) 95014

( * ) Notice: Subject to any disclaimer, the term of this patent is extended or adjusted under 35 U.S.C. 154(b) by 79 days.

(21) Appl. No.: 09/654,239

(22) Filed: Sep. 2, 2000

(51) Int. Cl.⁷ .......................... B67D 5/42; A61M 37/00
(52) U.S. Cl. ..................... 604/132; 222/386.5
(58) Field of Search .................. 222/386.5, 394; 604/132, 131, 153

(56) References Cited

U.S. PATENT DOCUMENTS 4,337,769 A * 7/1982 Olson .................. 222/386.5 X
5,713,865 A * 2/1998 Manning et al. ............ 604/122
5,961,487 A * 10/1999 Davis

* cited by examiner

Primary Examiner—William Wayner
(74) Attorney, Agent, or Firm—Show-Way Yeh

(57) ABSTRACT

The medicine reservoir contains medicine and a bag and may have flat or any other shape. A user programmable controller controls a pump on when and how much air or any kind of fluid is pumped into the bag. The bag then presses the same volume of medicine out of the reservoir into the user's body at approximately the same time. Pumping air requires little power so that the pump and the batteries have small weight and size. Hence, the apparatus is light, small, and flat to be attached to the user. The user feels like to use a large Band-Aid.

5 Claims, 3 Drawing Sheets

The conceptual structure of a flat medicine delivery device.

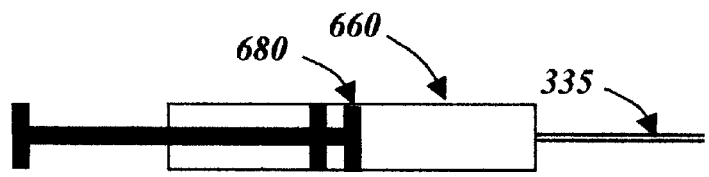
Fig. 1: A conventional syringe.
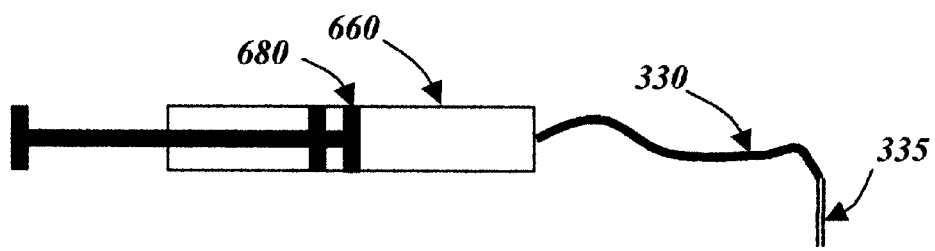
Fig. 2: The reservoir and the needle of an insulin pump.
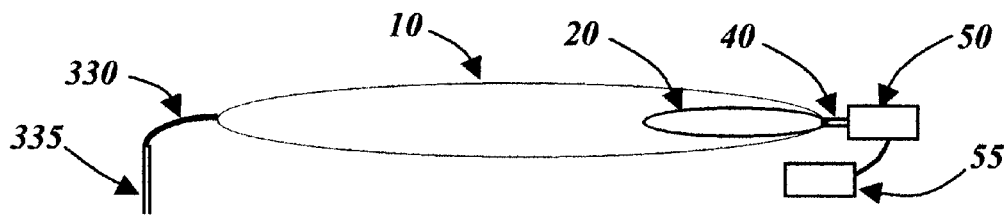
Fig. 3: The conceptual structure of a flat medicine delivery device.

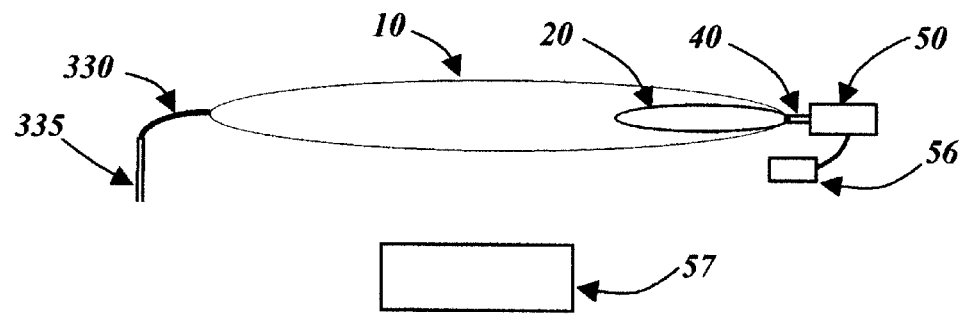
Fig. 4: The flat medicine delivery device with remote controller.
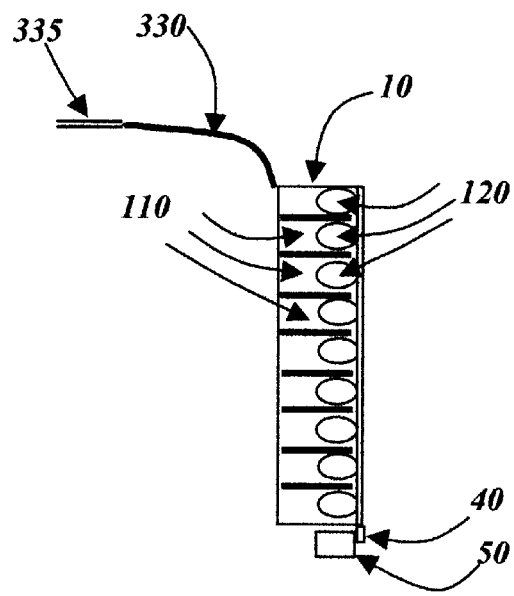
Fig. 5: The flat medicine delivery device with many cells.

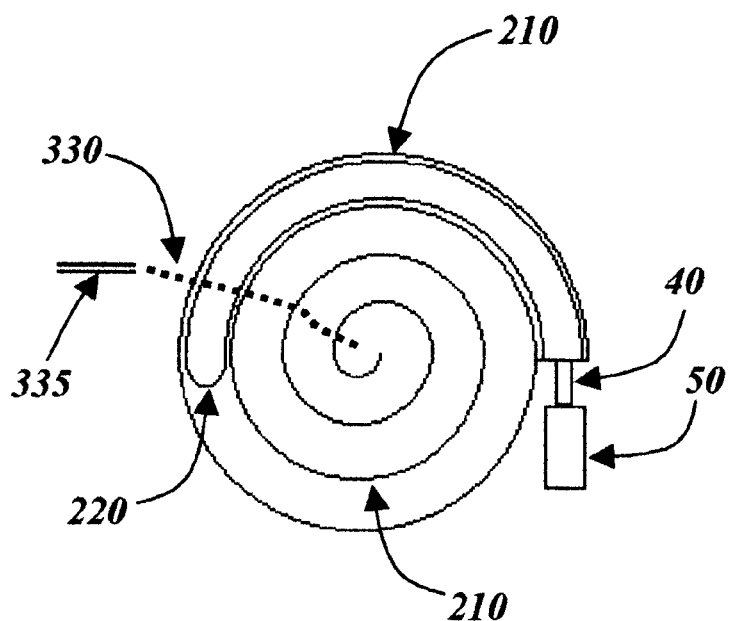
Fig. 6: The flat medicine delivery device with curly inside.

US 6,485,463 B1

MEDICINE DELIVERY APPARATUS WITH FLAT RESERVOIR

FIELD OF INVENTION

The present invention relates to medicine delivery systems to deliver medicine into the user's body.

BACKGROUND

The medicine reservoirs of all syringes currently in the market have cylinder shapes as FIG. 1 shows. The reservoir 660 has cylinder shape. The medicine is held in the space of the reservoir 660. When the piston 680 is pressed, the medicine flows through the needle 335 into the user's body.

For the medicine users who need the medicine constantly and frequently, pumps are used. The insulin pumps are an example. A pump contains a programmable controller and monitor and a fluid pump and its associated parts. A reservoir containing medicine is installed in the pump. The controller and monitor accepts the user's command of how to deliver the medicine and display the information. FIG. 2 shows the reservoir. There is a pipe 330 that links the reservoir 660 and the cannula 335. The cannula 335 is a soft small pipe and is inserted into the user's body. The fluid pump presses the piston 680 to press the medicine to flow into the user's body through the pipe 330 and the cannula 335. The user is connected with the pump to receive the medicine. For this kind of medicine delivery devices, the reservoirs have the following disadvantages:

They are thick when attached to the patient's body;

The piston must be very tied to prevent from leaking. Hence, the friction between the piston and the reservoir body is large and the piston requires large power to move. Consequently, the size and the weight of The fluid pump and the batteries are large to be attached to the body.

Hence, the pump is too heavy, too thick, and too large to be attached to the users. The users must carry the pump that is an extra object to them. They feel very inconvenient to be connected to the pump via a pipe.

The U.S. Pat. No. 4,337,769 issued to Olson and the like are apparatuses that are not intended to be attached to the user or be carried under the user's clothes. The pressure on the medication bag is pre-installed before the apparatus is used. The outflow of the medication is controlled by valve means. The present invention is an apparatus that can be attached to the user or be carried under the user's clothes. The pressure on the medication bag is built by pumping the fluid, usually it is the air, into the housing when the dosage of the medication is dynamically determined. The dosage changes from time to time and, hence, the amount of the fluid pumped into the housing is determined dynamically. The outflow of the medication is determined accordingly because the amount of the medication pressed out is proportional to the volume of the fluid pumped in.

The U.S. Pat. No. 5,713,865 issued to Manning Et. Al., and the like are apparatuses to eliminate the air bubbles from the intravenous-fluid delivery system that intravenously injects fluid into a patient. They are not the medication infusion systems. They are not intended to be carried under the user's clothes or to be attached to the user's skin, either.

Although the title of the U.S. Pat. No. 5,961,487 issued to Davis is "Infusion Device with Audible Data Output", the invention is the means to audit or to annunciate the data of the medication infusion systems. It is not the medication infusion system. It is not intended to be carried under the user's clothes or to be attached to the user's skin, either.

OBJECTS AND ADVANTAGES

My invention is to overcome the above disadvantages so that the device connected to the user's body is light, small, and flat enough to be attached to the skin of the users. For example, use adhesive tape to do it. The users will feel like to use a BandAid. Or, use bend to tie the device to the body. They will not feel that they are connected to an extra object and feel much more convenient.

DRAWING FIGURES

FIG. 1: A conventional syringe.

FIG. 2: The reservoir of an insulin pump.

FIG. 3: The conceptual structure of a flat medicine delivery device.

FIG. 4: The flat medicine delivery device with remote controller.

FIG. 5: The flat medicine delivery device with small cells.

FIG. 6: The flat medicine delivery device with curly inside.

REFERENCE NUMERALS IN DRAWINGS

The number that is larger than 600 refers to a device only in conventional apparatus. The number that is between 300 and 600 refers to a device that is in both the apparatus of my invention and in conventional apparatus. The number that is smaller than 300 refers to a device only in the apparatus of my invention.

10: The medicine reservoir having arbitrary shape.

20: The bag in the reservoir.

40: The pipe and valve that connects the bag and the fluid pump.

50: The fluid pump to pump the fluid into the bag.

55: The programmable controller of the medicine deliver apparatus.

56: The fluid pump controller that controls the fluid pump how to pump the fluid.

57: The monitor of the medicine deliver apparatus.

110: The small cells in the reservoir.

120: The small bags in the cells.

210: The reservoir having curly tunnel.

220: The bag in the curly tunnel reservoir.

330: The pipe that links the medicine reservoir and the needle or the cannula.

335: The needle or the cannula of the medicine deliver apparatus.

660: The medicine reservoir of a conventional medicine deliver apparatus having cylinder shape.

680: The piston of a conventional medicine deliver apparatus.

SUMMARY

My invention includes a medicine reservoir that has arbitrary shaped and may be divided into small cells. The reservoir or each cell contains a bag. The bags are pumped finite amount of fluid at the right time according to the user's desire. Usually, the fluid is the air. The bags then press out the medicine into the user's body.

DESCRIPTION

FIG. 3 shows the conceptual structure of my invention. The reservoir 10 is flat to be conveniently attached to the patient's body or carried under the user's clothes. A pipe 330 links the reservoir 10 and the cannula or the needle 335 that inserts into the user's body. The medicine is delivered from the reservoir 10 into the patient's body through the pipe 330 and the cannula or the needle 335. There is a bag 20 in the reservoir 10. The bag 20 is connected to a fluid pump 50 through a pipe 40. A programmable controller 55 controls the fluid pump 50 to pump finite volume of fluid into the bag 20. When the fluid pump 50 pumps finite volume of fluid into the bag 20, the same volume of the medicine is pressed out of the reservoir 10 into the patient's body through the pipe 330 and the cannula or the needle 335. Usually the fluid is the air. However, when the apparatus gets wet, water may be pumped in the bag 20. Therefore, in general, any kind of fluid can be used as long as the volume is finite and is controllable.

Comparing to the conventional injection device and the pumps, the dimension of the piston in the fluid pump 50 is much smaller. Hence, the friction of the piston is much smaller. Consequently, it requires significantly less force to drive the piston. So, the size and the weight of the motor that drives the fluid pump 50 can be significantly smaller. Therefore, the device can be much lighter and smaller than the conventional ones. In additional, the reservoir 10 can be flat. Hence, it is much convenient to be taped or tied to the user or carried under the user's clothes.

Variations

The controller 55 can be divided into two parts: the fluid pump controller 56 and the monitor 57 as shown in FIG. 4. The fluid pump controller 56 and the monitor 57 can communicate with each other via any kind of channel, including wireless. The fluid pump controller 56 accepts commands from the monitor 57 and controls the fluid pump 50 how to pump the fluid and reports information to the monitor 57. The monitor 57 accepts commands from the user, sends the commands of how to pump to the fluid pump controller 56, accepts information reported from the fluid pump controller 56, and shows information to the user. Then, the monitor 57 may not be attached to the user's body. So, the device attached to the user's body can be smaller and the user is more convenient to use it.

When the user jumps or exercises, the medicine in the reservoir is shacked. That may cause bubbles in the medicine. The present invention discloses three ways to significantly reduce the effect.

The reservoir 10 may be divided into many small cells 110 as FIG. 5 shows. All cells are linked so that the medicine in all cells can flow out through the pipe 330 into the user's body. Each cell has a small bag 120. The small bag 120 has the same or very close shape and volume as the inside of the cell containing it when it is fully pumped. All small bags 120 are linked so that, when fluid is pumped in, the fluid can spread to all small bags 120. Depending on the amount of the medicine to be used, the cells 110 in the reservoir 10 are filled with the medicine and the small bags 120 contain any amount of fluid, including zero. When the fluid pump 50 pumps finite volume of fluid into the small bags 120, the same volume of the medicine is pressed out of the reservoir 10 into the patient's body through the pipe 330 and the cannula or the needle 335. The cells 110 and the small bags 120 can be small so that, when the whole device is shacked, very limited bubbles may occur. Again, the fluid is mainly the air.

The second way to prevent from causing bubbles in the medicine is to make the inside of the reservoir to be a narrow tunnel. For example, the inside of the reservoir 10 is a curly tunnel 210 as FIG. 6 shows. The wall of the curly tunnel 210 may have small holes so that the medicine can drift all around the space. The bag 220 is in the curly tunnel 210 and has the same or very close shape and volume as the inside of the curly tunnel 210 when the bag 220 is fully pumped. Depending on the amount of the medicine to be used, the curly tunnel 210 is filled with the medicine and the bag 220 contains any amount of fluid, including zero. When the fluid pump 50 pumps finite volume of fluid into the bag 220, the same volume of the medicine is pressed out of the reservoir 10 into the patient's body through the pipe 330 and the cannula or the needle 335. The tunnel 210 and the bag 220 can be very narrow so that, when the whole device is shacked, very limited bubbles may occur. Again, the fluid is mainly the air.

Another way to prevent from causing bubbles in the medicine is to combine the above two methods. Where each small cell 110 in FIG. 5 is a narrow curly tunnel as 210 in FIG. 6. The small bag 120 in FIG. 5 has the same or very close shape and volume as the inside of the curly tunnel containing it when it is fully pumped. The operation is the same as above.

Conclusion

My invention includes a medicine reservoir that has arbitrary shape and may be divided into small cells. The reservoir or each cell contains a bag. The fluid pump pumps finite amount of fluid at the right time according to the user's desire. The bags then press out the medicine into the user's body. The fluid is usually just the air.

Since pumping fluid into bags requires much less power than pressing the piston of the convention medicine reservoir, the fluid pump and the battery of my invention are much lighter and smaller than the conventional ones. Dividing the controller into two parts, the part to control the fluid pump is small and light, too. Additionally, the reservoir can be flat. Hence, the apparatus of my invention that is attached to the user's body is light, small, and flat so that the users will feel much more comfortable and convenient to use it.

I claim:

1. A medicine delivery for use with an infusion set apparatus that can be carried under the user's clothes or be attached to the user's skin, comprising:

installing a medicine reservoir that is flat and is filled with medicine;

installing a medicine pipe that connects said reservoir and the infusion set;

installing a bag that is in said medicine reservoir and contains air or water;

installing a fluid pump that can pump finite amount of air or water;

installing a fluid pipe that connects said bag and the outlet of said fluid pump; and installing a controller that accepts commands from the user and issues commands to said fluid pump to control said fluid pump to pump finite amount of fluid into said bag at the moments of time according to the user's desire and displays information to the user;

so that said medicine delivery apparatus can be light, small, and flat, and, hence, can be attached to the user or carried under the user's clothes; the user can program how to deliver the medicine; appropriate amount of air or water is pumped into said bag via said fluid pipe at the appropriate moments of time; and appropriate amount of the medicine is pressed out from said reservoir into the user's body via said medicine pipe and said infusion set.

2. The medicine delivery apparatus of claim 1 wherein:

said reservoir is divided into many cells and the medicine can drift through all said cells;

said bag is divided into small bags where each said cell contains one said small bag, the fluid can freely flow through all said small bags, and each said small bag has the same or similar shape and volume as the inner side of the cell containing said small bag when said small bag is fully pumped;

so that limited number of bubbles can result from shacking said medicine delivery apparatus.

3. The medicine delivery apparatus of claim 1 wherein:

said reservoir is a narrow tunnel to contain the medicine and the medicine can drift through all space of said narrow tunnel;

said bag is in said narrow tunnel and has the same or similar shape and volume as the inner side of said narrow tunnel when said bag is fully pumped;

so that limited number of bubbles can result from shacking said medicine delivery apparatus.

4. The medicine delivery apparatus of claim 2 wherein:

each of said cells is a small narrow tunnel to contain the medicine and the medicine can drift through all space of said medicine reservoir;

each of said small bags is in one of said small narrow tunnels where the fluid can freely flow through all said small bags and each said small bag has the same or similar shape and volume as the inner side of the small narrow tunnel containing said small bag when said small bag is fully pumped;

so that limited number of bubbles can result from shacking said medicine delivery apparatus.

5. The medicine delivery apparatus of claims 1, 2, 3, and 4 wherein:

said controller is divided into two linked parts, the fluid pump controller and the monitor that can communicate with each other through any kind of communication channel;

said monitor accepts commands from the user, issues commands to said fluid pump controller, receives information from said fluid pump controller, and displays information to the user; and said fluid pump controller accepts commands from said monitor, controls said fluid pump to pump right amount of fluid into said bag or said small bags at the right time, detects all necessary information, and send said information to said monitor;

so that the weight and the size of the part of said medicine delivery apparatus to be attached to the user can be lighter and smaller, respectively, and the user is easier to program and to see the display.

\* \* \* \* \*